(12) United States Patent  
Huang (10) Patent No.: US 11,870,395 B2  
(45) Date of Patent: Jan. 9, 2024

(54) DETECTION CIRCUIT FOR CONNECTION IMPEDANCE AND ELECTRONIC DEVICE

(71) Applicant: SHANGHAI YAOHUO MICROELECTRONICS Co., Ltd., Shanghai (CN)

(72) Inventor: Lei Huang, Beijing (CN)

(73) Assignee: SHANGHAI YAOHUO MICROELECTRONICS Co., Ltd., Shanghai (CN)

( * ) Notice: Subject to any disclaimer, the term of this patent is extended or adjusted under 35 U.S.C. 154(b) by 430 days.

(21) Appl. No.: 17/378,735

(22) Filed: Jul. 18, 2021

(65) Prior Publication Data

US 2022/0255505 A1    Aug. 11, 2022

(30) Foreign Application Priority Data

Feb. 5, 2021    (CN) .......................... 202110163023.4

(51) Int. Cl.
| | |
|---|---|
| *H03F 1/02* | (2006.01) |
| *H03F 3/45* | (2006.01) |
| *H03F 1/56* | (2006.01) |
| *A61B 5/053* | (2021.01) |

(52) U.S. Cl.
CPC .............. *H03F 1/02* (2013.01); *A61B 5/053* (2013.01); *H03F 1/56* (2013.01)

(58) Field of Classification Search
CPC ..... H03F 1/02; H03F 1/56; H03F 3/72; H03F 2200/261; H03F 2203/45536; H03F 2203/45592; H03F 2203/7233; H03F 2203/7239; H03F 3/45475; A61B 5/053
USPC ........................................... 330/51, 252–261
See application file for complete search history.

(56) References Cited

U.S. PATENT DOCUMENTS

| | | | |
|---|---|---|---|
| 6,496,721 B1 * | 12/2002 | Yonce .................... | A61B 5/308 600/509 |
| 10,416,193 B2 * | 9/2019 | Kim ...................... | H03H 11/126 |

* cited by examiner

*Primary Examiner* — Hieu P Nguyen  
(74) *Attorney, Agent, or Firm* — NZ CARR LAW OFFICE (57) ABSTRACT

The present invention provides a detection circuit for a connection impedance and an electronic device. The detection circuit includes: a detection operational amplifier module, wherein the detection operational amplifier module includes: a first buffer, a switch unit, and a main operational amplifier; a first input terminal of the first buffer is connected to a first acquisition electrode through a first front-end circuit, an output terminal of the main operational amplifier is connected to a back-end circuit, and an output terminal of the first buffer is connected to a second input terminal of the first buffer; a first terminal of the switch unit is directly or indirectly connected to the first front-end circuit, and a second terminal of the switch unit is connected to the back-end circuit; and the switch unit is configured to: control the first front-end circuit to be directly connected to the back-end circuit, to form a straight-through channel.

20 Claims, 4 Drawing Sheets

DETECTION CIRCUIT FOR CONNECTION IMPEDANCE AND ELECTRONIC DEVICE

CROSS REFERENCE

This application is related to and claims priority to CN Application No. 202110163023.4 entitled "DETECTION CIRCUIT FOR CONNECTION IMPEDANCE AND ELECTRONIC DEVICE" filed on Feb. 5, 2021 is herein incorporated by reference in its entireties and all purposes.

TECHNICAL FIELD

The present invention relates to an electronic device, and in particular, to a detection circuit for a connection impedance and an electronic device.

BACKGROUND

With the wide application of wearables such as smart watches and bands, wireless Bluetooth headsets, electrocardiogram patches and other products, there are increased concerns about adding detection of human body bioelectric signals or optimizing acquisition quality of human body bioelectric signals. Given that a human body impedance plus a contact impedance between an acquisition electrode of a product and the skin, or the like is relatively large, for example, up to 100 million Ω (100 MΩ), bioelectric signals usually need to be inputted to an input buffer with a larger input impedance (for example, implemented by an operational amplifier with an extremely low input leakage current) for impedance transformation, and then inputted to a subsequent signal acquiring and processing circuit.

Devices supporting bioelectric signal acquisition (such as smart watches) are especially focused on power saving processing of a system. Therefore, before an object to be tested is connected (for example, a finger of a human body contacts an acquisition electrode, and an IN+ pin and an IN− pin are respectively connected to two different acquisition electrodes), signal acquisition circuit and processing circuit parts of such type of products are in a low-power standby mode, and therefore a low-power detection path for connecting to an object to be tested is needed to help monitor the connection of the object to be tested in real time, so as to trigger acquisition of bioelectric signals. Further, a detection circuit for a connection impedance needs to be employed.

In the related prior art, a detection circuit for a connection impedance may adopt a detection operational amplifier module. However, excessively high power consumption is caused if the detection operational amplifier module is always in an operating state.

SUMMARY

The present invention provides a detection circuit for a connection impedance and an electronic device, to resolve the problem of excessively high power consumption.

A first aspect of the present invention provides a detection circuit for a connection impedance, including: a detection operational amplifier module, wherein the detection operational amplifier module includes: a first buffer, a switch unit, and a main operational amplifier;

a first input terminal of the first buffer is connected to a first acquisition electrode through a first front-end circuit, an output terminal of the main operational amplifier is connected to a back-end circuit, and an output terminal of the first buffer is connected to a second input terminal of the first buffer;
a first terminal of the switch unit is directly or indirectly connected to the first front-end circuit, and a second terminal of the switch unit is connected to the back-end circuit; and
the switch unit is configured to: control the first front-end circuit to be directly connected to the back-end circuit, to form a turned-on straight-through channel, or control the straight-through channel to be turned off, where the main operational amplifier stops operating when the turned-on straight-through channel is formed.

Optionally, the detection operational amplifier module further includes: a first electro-static discharge unit; and the first input terminal and the second input terminal of the first buffer are further grounded through the first electro-static discharge unit. Optionally, the switch unit includes a first switch, a second switch, and a third switch; a first terminal of the first switch is connected to the output terminal of the first buffer, a first terminal of the second switch is connected to the first front-end circuit and the first input terminal of the first buffer, a second terminal of the second switch is connected to a first terminal of the third switch, a second terminal of the third switch is connected to the back-end circuit, and a second terminal of the first switch is connected to a connection point between the second switch and the third switch.

Optionally, the detection operational amplifier module further includes: a logic processing unit; and the logic processing unit is connected to a controlled terminal of the first switch, a controlled terminal of the second switch, and a controlled terminal of the third switch.

Optionally, an enable terminal of the main operational amplifier and the switch unit are connected to a logic processing unit.

Optionally, the logic processing unit is configured to:
if being controlled in a first mode, control the straight-through channel to be turned off, and disable a function of the main operational amplifier;
if being controlled in a second mode, enable a function of the main operational amplifier, and control the straight-through channel to be turned off; or
if being controlled in a third mode, control the straight-through channel to be turned on, and disable a function of the main operational amplifier.

Optionally, the detection circuit for a connection impedance further includes a control module, where the logic processing unit is connected to the control module, to enter a corresponding mode in response to a control signal sent by the control module.

Optionally, the detection circuit for a connection impedance further includes a control module, the control module being configured to directly or indirectly control an enable terminal of the main operational amplifier, and the switch unit, where the control module is specifically configured to:
in a case that the turned-on straight-through channel is formed and the main operational amplifier stops operating, if the turned-on straight-through channel detects that there is an object to be tested being connected to the first acquisition electrode, control the straight-through channel to be turned off, and control the main operational amplifier to be enabled. Optionally, the detection operational amplifier module further includes a second buffer and a second electro-static discharge unit;
a first input terminal of the second buffer is connected to a second acquisition electrode through a second front-end circuit, and an output terminal of the second buffer is connected to a second input terminal of the second buffer; and the first input terminal and the second input terminal of the second buffer are further grounded through the second electro-static discharge unit.

Optionally, the first buffer and the second buffer each are a unity gain buffer. Optionally, the detection operational amplifier module is disposed in a same chip.

A second aspect of the present invention provides an electronic device, including the detection circuit for a connection impedance described in the first aspect and the optional solutions thereof.

In the detection circuit for a connection impedance and the electronic device provided in the present invention, a switch unit is integrated in the detection operational amplifier module and the switch unit may control the first front-end circuit to be directly connected to the back-end circuit, to form the turned-on straight-through channel, or may control the straight-through channel to be turned off. The present invention implements switching between being directly connected and functionality of the main operational amplifier. When the straight-through channel is turned off, it is convenient to perform buffering and feedback on a detected signal during normal detection, and forming of the turned-on straight-through channel may help detect, in a low power consumption state for example, whether there is an object to be tested being connected (i.e., providing a straight-through channel for implementing the detection). Further, because the main operational amplifier is not operating when the turned-on straight-through channel is formed, the present invention can effectively reduce the power consumption, compared with the solution in which the main operational amplifier is always operating. Moreover, if the switch unit does not adopt an independent analog switch, a response speed can be effectively increased, so that the circuit participates in a detection and feedback process for an object to be tested as soon as possible. In addition, the present invention can effectively reduce solution costs and an area of a system circuit board while ensuring the implementation of the function.

In a further optional solution, a logic processing unit is used in the detection operational amplifier module for controlling. Enabling of the main operational amplifier, on/off of the switch, and the like are all implemented by the logic processing unit in the detection operational amplifier module, and further there is no need to adopt a plurality of pins, thereby effectively reducing overheads of pin resources.

In a further optional solution, namely, the solution based on the first switch, the second switch, and the third switch, when the second switch is turned off, a voltage difference between two terminals of the second switch is extremely small (for example, 1 mV). Because no independent switch chip is adopted, a large turned-on resistance (for example, 100 KΩ) switch (the second switch) may be especially designed and integrated, to further ensure that a turned-off impedance reaches a larger level (for example, a level of 10 GΩ) when the second switch is turned off, thereby implementing minimization of a turned-off leakage current of the channel of the second switch. Further, an entire input leakage current of the detection operational amplifier module during operating is ensured to be minimized.

DESCRIPTION OF THE DRAWINGS

To explain the embodiments of the present invention or the technical solutions of the prior art more clearly, the accompanying drawings to be used in the description of the embodiments or the prior art will be briefly described below. Clearly, the accompanying drawings in the following description are only some embodiments of the present invention, and a person of ordinary skill in the art may further obtain other drawings based on these accompanying drawings without creative efforts.

REFERENCE NUMERALS

Detection operational amplifier module;
    10—Chip;
    11—Switch unit;
    S1—First switch;
    S2—Second switch;
    S3—Third switch;
    12—Main operational amplifier;
    13—First buffer;
    14—First electro-static discharge unit;
    Tr1—First electro-static trigger switch;
    ESD1—First electro-static discharge device;
    15—First buffer;
    16—Second electro-static discharge unit;
    Tr2—Second electro-static trigger switch;
    ESD2—Second electro-static discharge device;
    17—Logic processing unit; and
Control module.

DESCRIPTION OF EMBODIMENTS

The following clearly and completely describes the technical solutions in the embodiments of the present invention with reference to the accompanying drawings of the embodiments of the present invention. Clearly, the embodiments described are merely some embodiments, other than all embodiments, of the present invention. All other embodiments obtained based on the embodiments of the present invention by a person of ordinary skill in the art without creative efforts shall fall within the protection scope of the present invention.

The terms "first", "second", "third", "fourth," and the like, if existent, in the specification, claims, and the accompanying drawings of the present invention are used to distinguish between similar objects and are not intended to describe a particular order or precedence. It should be understood that the terms used in such way are interchangeable where appropriate, so that the embodiments of the present invention described herein can be practiced in order other than those illustrated or described herein. In addition, the terms "comprise/include" and "have" and any variations thereof are intended to cover a non-exclusive meaning, for example, processes, methods, systems, products, or devices including a series of steps or units are not necessarily limited to those steps or units clearly listed, but may include other steps or units that are not explicitly listed or inherent to such processes, methods, products, or devices.

The technical solutions of the present invention are described in detail below with specific embodiments. The following specific embodiments may be combined with each other, and the same or similar concepts or processes may not be repeated in some embodiments.

Figure 1:
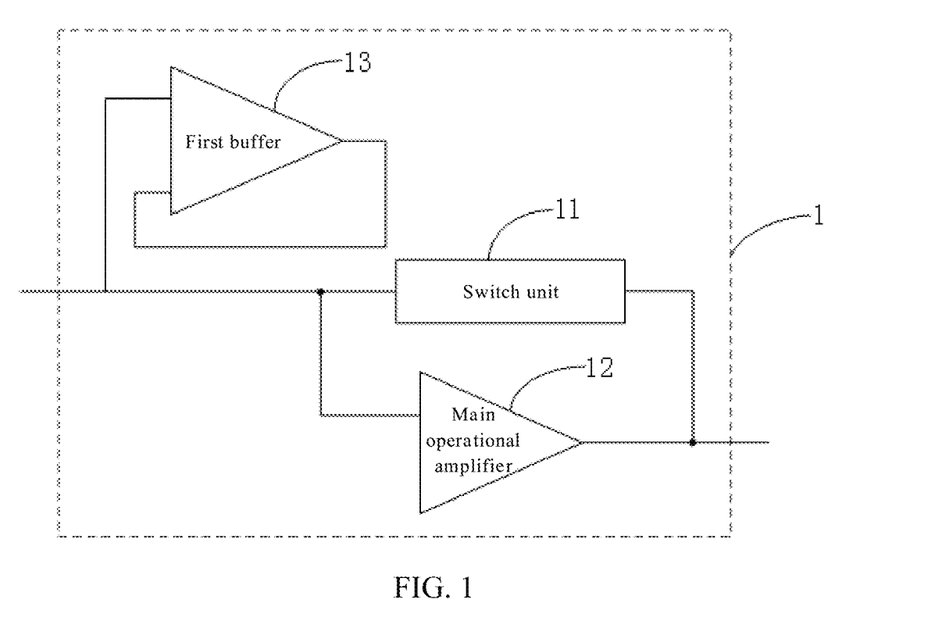
FIG. 1 is schematic structural diagram 1 of a detection circuit for a connection impedance according to an embodiment of the present invention.
Figure 2:
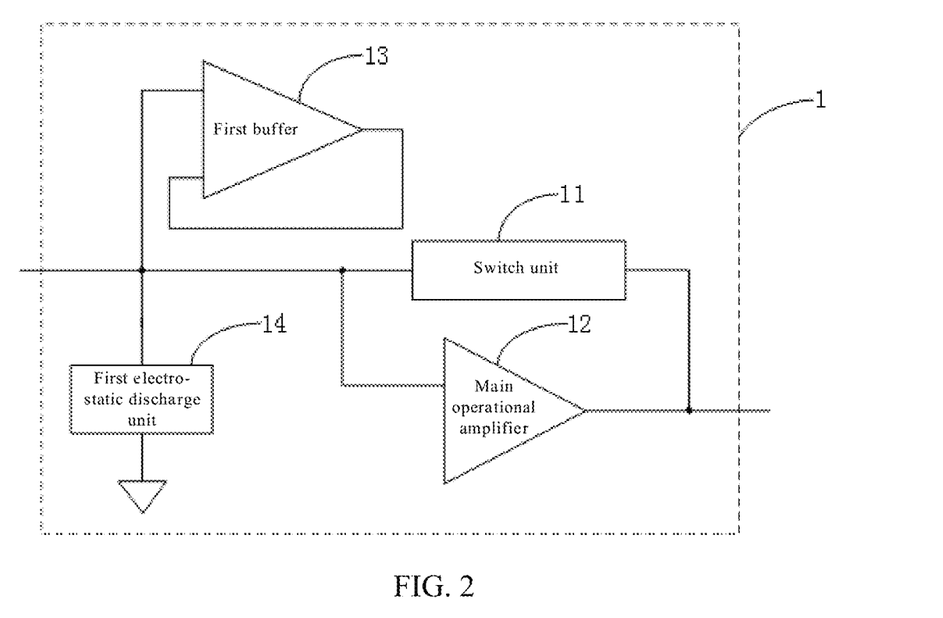
FIG. 2 is schematic structural diagram 2 of a detection circuit for a connection impedance according to an embodiment of the present invention.

Referring to FIG. 1, a detection circuit for a connection impedance includes: a detection operational amplifier module 1. The detection operational amplifier module 1 includes: a first buffer 13, a switch unit 11, and a main operational amplifier 12.

Wherein the connection impedance may be any object that may be regarded as an impedance of the circuit. Further, the connection impedance may be understood as a high impedance, for example, an impedance formed due to detection of connection of a bioelectric signal, an impedance formed due to detection of a gas sensor signal, or the like. Further, the circuit in the embodiments of the present invention may implement detection of connection of a high impedance and impedance transformation.

Wherein an acquisition electrode, which may be a metallic contact exposed out of an electronic device such as a smart watch, is configured to measure a bioelectric signal or the like. Such a type of contact is generally connected to a non-inverting input terminal (i.e., an IN+ pin) or an inverting input terminal (i.e., an IN− pin) of the signal detection operational amplifier module 1.

A first input terminal of the first buffer 13 is connected to a first acquisition electrode through a first front-end circuit, an output terminal of the main operational amplifier 12 is connected to a back-end circuit, and an output terminal of the first buffer 13 is connected to a second input terminal of the first buffer 13.

Wherein the first input terminal of the first buffer 13 may be a non-inverting input terminal and the second input terminal thereof may be an inverting input terminal.

The first front-end circuit may be understood as any circuit connected to the first buffer 13 and the first acquisition electrode, and wherein any device or device combination may be provided therein. Meanwhile, if the detection operational amplifier module 1 is disposed in a same chip, the first front-end circuit may be provided with a pin (for example, an N+ pin) corresponding to the chip. Specifically, the first acquisition electrode may be a positive acquisition electrode.

A first terminal of the switch unit 11 is directly or indirectly connected to the first front-end circuit, and a second terminal of the switch unit 11 is connected to the back-end circuit. Further, the switch unit is configured to: control the first front-end circuit to be directly connected to the back-end circuit, to form a straight-through channel, or control the straight-through channel to be turned off. Further, the switch unit 11 may be controlled to selectively form or turn off the straight-through channel.

During control over the switch unit 11, enabling of the main operational amplifier 12 may further be controlled. For example, when the straight-through channel is turned off, the main operational amplifier 12 is controlled to be enabled, to perform a function of signal amplifying or transmitting. When the straight-through channel is connected (not turned off), the function of the main operational amplifier 12 is disabled, to perform a function of signal buffering or transmitting. That is, when the turned-on straight-through channel is formed, the main operational amplifier stops operating.

Wherein the switch unit 11 may be any device or device combination capable of implementing the foregoing functions, including a switch device connected in series between the first front-end circuit and the back-end circuit. On this basis, with diversity of the functions of the switch unit 11, the devices in the switch unit 11 are not limited thereto, and all variations made thereon do not depart from the scope of the embodiments of the present invention.

Wherein the main operational amplifier may also be represented as a main amplifier, and may be any device or device combination capable of implementing signal buffering (impedance transformation) and/or amplifying.

Wherein the functions of the straight-through channel may be for example: connecting a voltage source or a current source to an acquisition electrode (i.e., connecting to a high connection impedance of an object to be tested), or may be for example: acquiring a signal of a high connection impedance and transmitting the signal to the back-end circuit.

In a specific example, the detection circuit may further include a detection module. The detection module may be connected to the back-end circuit, a control module, and a voltage source or a current source. When the turned-on straight-through channel is formed, the detection module may be controlled by the control module to supply the voltage source or the current source to the back-end circuit, further to the acquisition electrode through the straight-through channel. Meanwhile, the detection module may detect information (for example, a voltage or a current) of an electric signal transmitted in the back-end circuit at this time, and directly or indirectly feed back the information to the control module, based on which the control module may determine whether there is an impedance being connected, and if there is an impedance being connected, control the straight-through channel to be turned off and enable the main operational amplifier, to further implement signal buffering and/or amplifying by using the main operational amplifier. The detection module may measure information (for example, a voltage or a current) of an electric signal transmitted in the back-end circuit at this time, based on which further analysis and determining (or other processing) are further performed. Further, the detection module may include, for example, a switch connected between the voltage source or the current source and the back-end circuit. The switch may be controlled by the control module, to further control whether to supply the voltage source or the current source to the acquisition electrode. The detection module may further include a current detection unit or a voltage detection unit, which may be connected between the control module and the back-end circuit, detect a voltage or a current in the back-end circuit at this time, and feed back the detected voltage or current to the control module.

The implementations of the detection module are not limited to the foregoing examples, and meanwhile some or all functions of the detection module may alternatively be implemented by being integrated in the control module. The existing or improved functions of the detection module or the control module in the art all fall within the scope of the embodiments of the present invention.

It can be seen that a switch unit is integrated in the detection operational amplifier module and the switch unit may control the first front-end circuit to be directly connected to the back-end circuit, to form the straight-through channel, or may control the straight-through channel to be turned off. The present invention implements switching between being directly connected and functionality of the operational amplifier. When the straight-through channel is turned off, it is convenient to perform input buffering and feedback on a detected signal during normal detection, and forming of the turned-on straight-through channel may help detect, in a low power consumption state for example, whether there is an object to be tested being connected (i.e., providing a straight-through channel for implementing the detection). Further, because the main operational amplifier is not operating when the turned-on straight-through channel is formed, the present invention can effectively reduce the power consumption, compared with the solution in which the main operational amplifier is always operating. Moreover, if the switch unit does not adopt an independent analog switch, a response speed can be effectively increased, so that the circuit participates in a detection and feedback process for an object to be tested as soon as possible. In addition, the present invention can effectively reduce solution costs and an area of a system circuit board while ensuring the implementation of the function.

Figure 5:
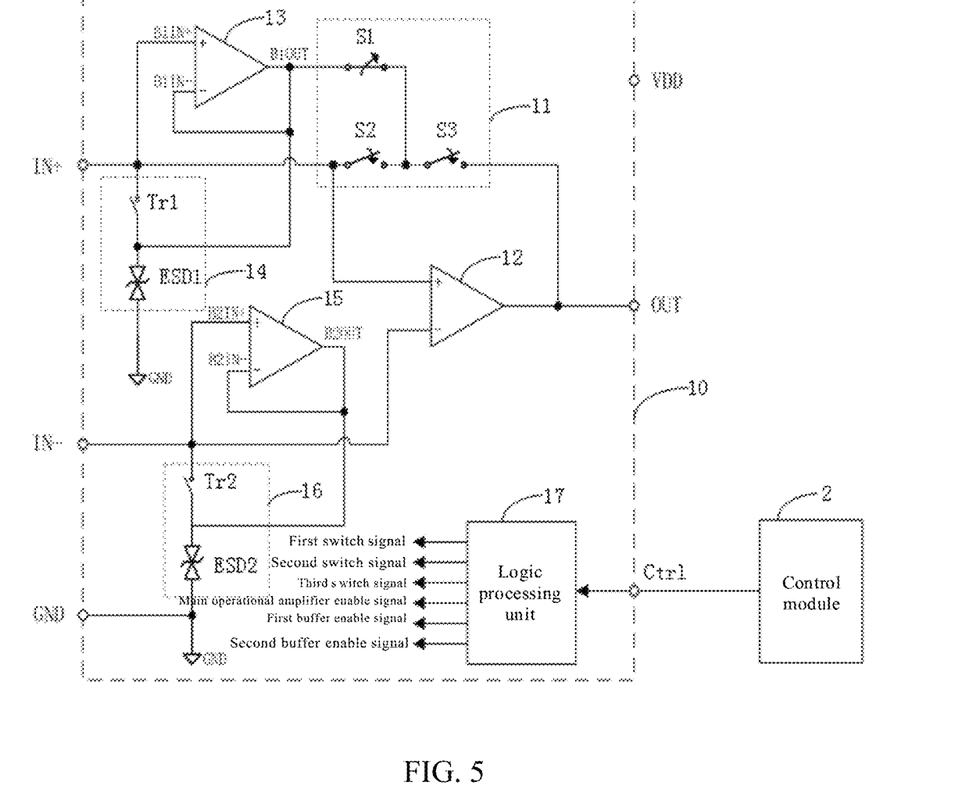
FIG. 5 is schematic structural diagram 5 of a detection circuit for a connection impedance according to an embodiment of the present invention.

In a specific solution, in combination with FIG. 5, if the circuit is mainly oriented to connection detection of a high impedance and signal impedance transformation (for example, detection of a bioelectric signal and detection of a gas sensor signal), there is a high requirement for an input impedance of the main operational amplifier for implementing output impedance transformation of a signal to be tested. For example, during testing of an electrocardiogram signal of a human body, when a finger of the human body contacts an electrode of a testing device (for example, a smart watch), a total impedance of an impedance of the object to be tested (the human body) and a contact impedance may be up to 100 M (100 million) Ω. Such a bioelectric signal may be extremely sensitive, and a signal input buffer needs to be added at a position nearest to the acquisition electrode, to implement impedance transformation.

In actual model selection, to reduce attenuation of a signal to be tested, a typical value of the input impedance of the main operational amplifier generally needs to be above 1 G (1 billion) Ω, which requires an input leakage current at the pins (for example, an IN+ pin and an IN− pin) of the front-end circuit to be as low as possible, so as to avoid reduction of the input impedance of the main operational amplifier (i.e., the operational amplifier).

To reduce system power consumption of such products (for example, a smart watch supporting detection of a bioelectric signal), the detection operational amplifier module (including the buffer and the main operational amplifier) and software and hardware parts (including, for example, the control module) for processing the bioelectric signal at the back-end usually both enter a low power mode when there is no bioelectric signal to be measured (when no finger manually presses the acquisition electrode). However, to enable the system to make a quick response when a finger manually presses the acquisition electrode for processing new measurement, a straight-through channel between the front-end circuit and the back-end circuit of the detection operational amplifier module needs to be established, so that the system circuit connects the monitored voltage source or the current source connected to a high connection impedance of the object to be tested through the straight-through channel, due to contact between the object to be tested (for example, a finger) and the acquisition electrode (for example, the IN+ pin) and then determines, based on a signal variation (for example, a voltage change) fed back to the system, whether there is an object to be tested being connected. If there is an object to be tested being connected, the main operational amplifier needs to be used to acquire and amplify the signal.

In an implementation, referring to FIG. 2 to FIG. 5, the detection operational amplifier module further includes: a first electro-static discharge unit 14; and the first input terminal and the output terminal of the first buffer 13 are further grounded through the first electro-static discharge unit 14.

Figure 4:
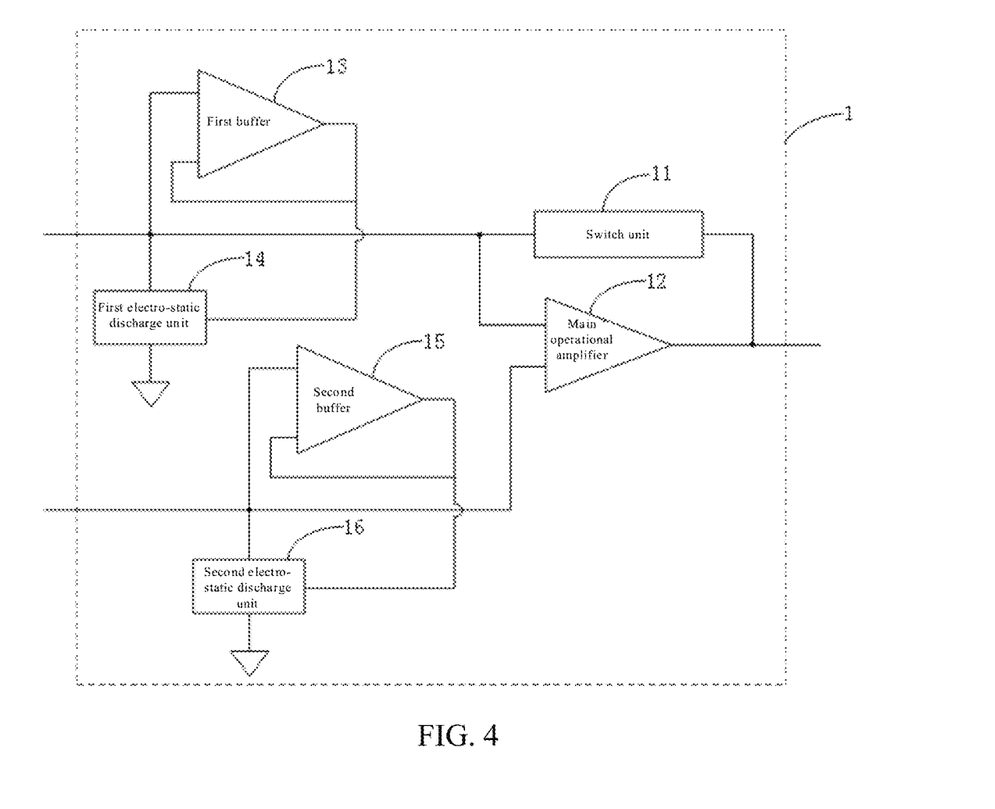
FIG. 4 is schematic structural diagram 4 of a detection circuit for a connection impedance according to an embodiment of the present invention.

In an implementation, the acquisition electrode includes a first acquisition electrode (which may be understood as a positive acquisition electrode) and a second acquisition electrode (which may be understood as a negative acquisition electrode). Further, the detection operational amplifier module 1 further includes a second buffer 15 and a second electro-static discharge unit 16.

A first input terminal of the second buffer 15 is connected to the second acquisition electrode through a second front-end circuit, and an output terminal of the second buffer 15 is connected to a second input terminal of the second buffer 15.

The first input terminal of the second buffer 15 may be a non-inverting input terminal and the second input terminal thereof may be an inverting input terminal.

The second front-end circuit may be understood as any circuit connected to the second buffer 15 and the second acquisition electrode, and any device or device combination may be provided therein. Meanwhile, if the detection operational amplifier module 1 is disposed in a same chip, the second front-end circuit may be provided with a pin (for example, an N− pin) corresponding to the chip. Specifically, the second acquisition electrode may be a negative acquisition electrode.

Further, referring to FIG. 4, the first input terminal and the second input terminal of the second buffer 15 are further grounded through the second electro-static discharge unit 16.

The first buffer and the second buffer each are a unity gain buffer.

Specifically, in the unity gain buffer, a signal gain that can be implemented by using an operational amplifier is 1, that is, a voltage buffer followed by output and input voltages.

Wherein the electro-static discharge unit may be understood as any device or device combination capable of implementing electro-static discharge, may be implemented by a combination of a diode and an electro-static discharge device in some solutions, or may be implemented by a combination of a switch and an electro-static discharge device.

Referring to FIG. 5, the first electro-static discharge unit 14 may include a first electro-static trigger switch Tr1 and a first electro-static discharge device ESD1. A first terminal of the first electro-static trigger switch Tr1 is connected to the first input terminal and the second input terminal of the first buffer 13. A second terminal of the first electro-static trigger switch Tr1 is grounded.

The second electro-static discharge unit 16 may include a second electro-static trigger switch Tr2 and a second electro-static discharge device ESD2. A first terminal of the second electro-static trigger switch Tr2 is connected to the first input terminal and the second input terminal of the second buffer 15. A second terminal of the second electro-static trigger switch Tr2 is grounded.

Wherein the electro-static trigger switch may be understood as a circuit switch which is normally in a turned-off state, may be quickly turned on upon an electro-static impact, and may alternatively be represented as: Trigger SW.

The electro-static discharge device may be represented as ESD.

In an implementation, referring to FIG. 5, the detection operational amplifier module 1 further includes: a logic processing unit 17. The logic processing unit 17 may be connected to a switch module 11 (for example, controlled terminals of the first switch S1, the second switch S2, and the third switch S3), an enable terminal of the main operational amplifier 12, an enable terminal of the first buffer 13, and an enable terminal of the second buffer 15.

Further, referring to FIG. 5, the circuit may further include a control module 2. The logic processing unit 17 may be connected to the control module 2, to enter a corresponding mode in response to a control signal sent by the control module, to further output a signal to the switch module 11, the enable terminal of the main operational amplifier 12, the enable terminal of the first buffer 13, and the enable terminal of the second buffer 15 under the control of the control module 2.

For example, the logic processing unit 17 may control the first switch S1 through a first switch signal; the logic processing unit 17 may control the second switch S2 through a second switch signal; the logic processing unit 17 may control the third switch S3 through a third switch signal; the logic processing unit 17 may further control the main operational amplifier 12 through an main operational amplifier enable signal; the logic processing unit 17 may further control the first buffer 13 through a first buffer enable signal; and the logic processing unit 17 may further control the second buffer 15 through a second buffer enable signal.

In an example, the detection operational amplifier module 1 may be disposed in a chip 10. The control module 2 may be disposed in another chip. In this case, the logic processing unit 17 may be connected to the control module 2 through a control pin (i.e., a Ctrl pin).

Wherein the logic processing unit 17 may be understood as a circuit unit that receives a high logic level signal or low logic level signal inputted to the circuit and then implements a corresponding circuit control output, and may be, for example, implemented by using a corresponding logic gate or logic gate combination according to logic control requirements. In addition, the signal level to be outputted can be changed randomly based on the control manner of the main operational amplifier, the switch, and the buffer (the unity gain buffer).

In the foregoing solution, a logic processing unit is used in the detection operational amplifier module for controlling. Wherein enabling of the main operational amplifier, on/off of the switch, and the like are all implemented by the logic processing unit in the detection operational amplifier module, and further there is no need to adopt a plurality of pins, thereby effectively reducing overheads of pin resources.

Figure 3:
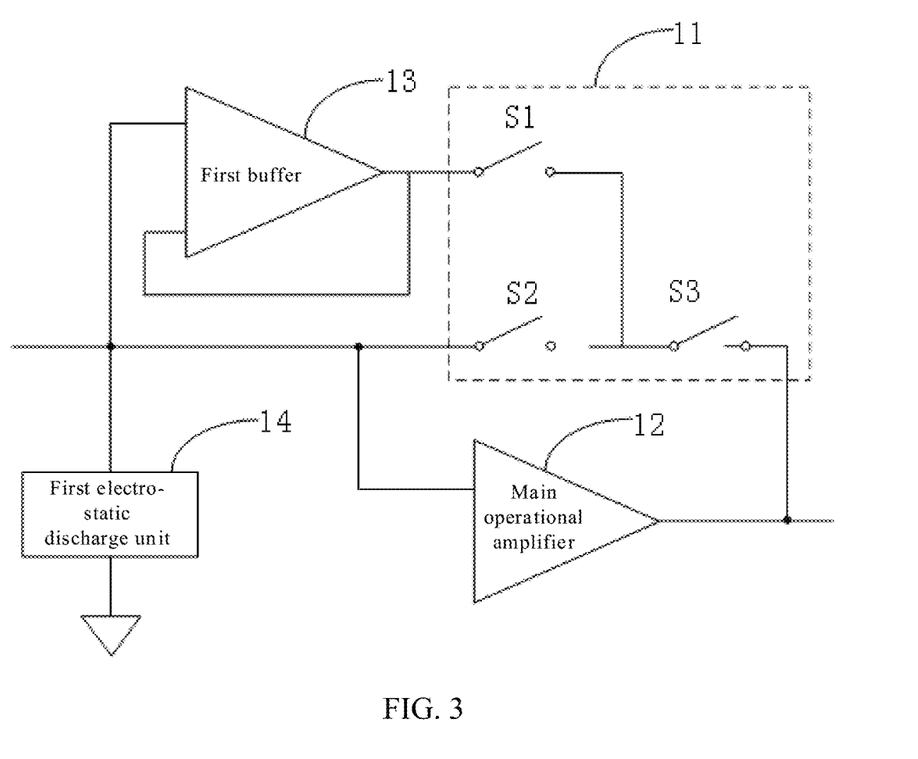
FIG. 3 is schematic structural diagram 3 of a detection circuit for a connection impedance according to an embodiment of the present invention.

In an implementation, referring to FIG. 3 and FIG. 5, the switch unit 1 includes a first switch S1, a second switch S2, and a third switch S3. A first terminal of the first switch S1 is connected to the output terminal of the first buffer 13, a first terminal of the second switch S2 is connected to the first front-end circuit and the first input terminal of the first buffer 13, a second terminal of the second switch S2 is connected to a first terminal of the third switch S3, a second terminal of the third switch S3 is connected to the back-end circuit, and a second terminal of the first switch S1 is connected to a connection point between the second switch S2 and the third switch S3.

Wherein the first switch S1, the second switch S2, and the third switch S3 may be any device, chip, or device combination capable of implementing on/off control, and may be, for example, implemented by using a transistor such as a field effect transistor, but the present invention is not limited thereto. In other examples, a changeover switch may alternatively be used to implement the functions of the first switch S1, the second switch S2, and the third switch S3.

In the foregoing solution, namely, the solution based on the first switch, the second switch, and the third switch, when the second switch is turned off, a voltage difference between two terminals of the second switch is extremely small (for example, 1 mV). Because no independent switch chip is adopted (i.e., the switch unit and the detection operational amplifier module are not in different chips), a large turned-on resistance (for example, 100 KΩ) switch may be integrated, to further ensure that a turned-off impedance reaches a larger level (for example, a level of 10 GΩ) when the second switch is turned off, thereby implementing minimization of a turned-off leakage current of the channel of the second switch. Further, an entire input leakage current of the detection operational amplifier module during operating is ensured to be minimized. In a specific example, referring to FIG. 5, when the main operational amplifier is needed to acquire and buffer a signal, the logic processing unit 17 may start the main operational amplifier 12 (which may also be understood as enabling the main operational amplifier 12) and turn off the second switch S2 and the third switch S3, to further perform corresponding signal acquisition (for example, acquisition of a bioelectric signal). During buffering of a high impedance signal input (i.e., impedance transformation), the second switch S2 and the third switch S3 need to be turned off, in order to turn off the straight-through channel (i.e., the straight-through channel between the IN+ pin and an OUT pin), so that the main operational amplifier 12 performs a normal input buffering function for a signal to be tested.

In this case, to minimize the impact on a leakage current at the IN+ pin in a case that the directly connected path constructed by the second switch S2 and the third switch S3 is turned off, the first switch S1 is added to the foregoing solution. The first switch S1 combines and reuses the first buffer 13 at the IN+ pin and configured to reduce a leakage current in the channel of the first electro-static discharge device ESD1, to greatly reduce a leakage current in a channel of the second switch S2. This may alternatively be understood as: in addition to that the first input terminal (i.e. B1 IN+ pin) and the second input terminal (i.e. B1 IN− pin) of the first buffer 13 are configured to act on two terminals of the first electro-static trigger switch Tr1 to reduce a voltage difference of the first electro-static trigger switch Tr1, so as to reduce a ground leakage current of the channel of the first electro-static discharge device ESD1, the first switch S1 (the first switch S1 is turned on when the second switch S2 and the third switch S3 are turned off) may further be used to connect the B1 IN− pin to a terminal of the second switch S2 (i.e., the connection point between the second switch S2 and the third switch S3), the other terminal of the second switch S2 is connected to the IN+ pin, and on the basis of application principles of such an operational amplifier as the unity gain buffer, a voltage difference between the B1 IN+ pin and the B1 IN− pin of the first buffer 13 is extremely small.

In a specific solution, in combination with an optional solution at a chip level, the voltage difference between the B1 IN+ pin and the B1 IN− pin may be controlled to be 1 mV or less. In addition, a turned-on resistance of the second switch S2 may be designed to be quite large (for example, typically 100 KΩ). In this way, a typical value of the impedance when the second switch S2 is turned off is up to 10 G (10 billion) Ω, so that a typical leakage current at the IN+ pin may be controlled to be approximately 1 mV/10 GΩ=0.1 pA when the channel composed of the second switch S2 and the third switch S3 is turned off.

In comparison, in a divisional solution of the analog switch and the detection operational amplifier module, the unity gain buffer cannot be reused to implement minimization of the voltage difference at two terminals of the switch, and a turned-on resistance of an existing analog switch chip is generally far less than 1 KΩ. Therefore, a typical equivalent turned-off impedance is approximately 100 MΩ, and thus a leakage current may reach a level of nA, thereby greatly impacting performance of the main operational amplifier when performing signal input buffering and transforming. Compared with the divisional solution, the specific solution of the present invention may make a compatible solution of compact and high-performance, high-impedance signal input buffering and high impedance connection detection be realistic and feasible. In addition, for the logic processing unit 17, as mentioned above, if only one control pin is used to interact outside with the control module, the logic processing unit may simultaneously control operating states of the first switch S1, the second switch S2, the third switch S3, the first buffer 13, the second buffer 15, and the main operational amplifier 12 based on control signals transmitted by the control pin.

In a further example, the logic processing unit 17 may implement the following three operating modes, to further switch between the three operating modes.

In a first mode, a function of a detection channel switch may be disabled (i.e. the second switch S2 and the third switch S3 are controlled to be turned off) and a function of the main operational amplifier 12 is also disabled, in which case it may be understood as that: the chip 10 (i.e., the detection operational amplifier module 1) enters a shutdown mode (i.e., a power-off mode). That is, the logic processing unit is configured to: if being controlled in the first mode, control the straight-through channel to be turned off, and disable the function of the main operational amplifier.

In a second mode, a function of the main operational amplifier 12 may be enabled and a function of a detection channel switch may be disabled (i.e., the second switch S2 and the third switch S3 are controlled to be turned off). That is, the logic processing unit is configured to: if being controlled in the second mode, enable the function of the main operational amplifier, and control the straight-through channel to be turned off.

In a third mode, a function of a detection channel switch may be enabled (i.e. the second switch S2 and the third switch S3 are controlled to be turned on) and a function of the main operational amplifier 12 is disabled. That is, the logic processing unit is configured to: if being controlled in the third mode, control the straight-through channel to be turned on and disable the function of the main operational amplifier.

The enabling and disabling of the function of the detection channel switch involved may be understood by referring to the on and off of the straight-through channel described in the foregoing context.

Therefore, the control module is configured to directly or indirectly control an enable terminal of the main operational amplifier, and the switch unit (for example, implementing control by using the logic processing unit), where the control module is specifically configured to:

in a case that the turned-on straight-through channel is formed and the main operational amplifier stops operating, if the turned-on straight-through channel detects that there is an object to be tested being connected to the first acquisition electrode, control the straight-through channel to be turned off, and control the main operational amplifier to be enabled.

Figure 6:
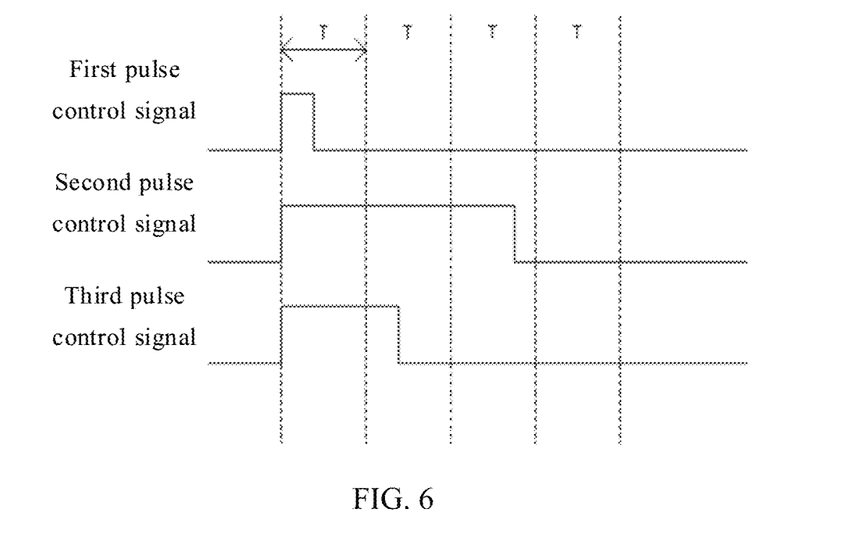
FIG. 6 is schematic diagram of a control signal according to an embodiment of the present invention.

In a specific solution, between the control module and the logic processing unit, different pulse widths of control signals may be used to instruct the logic processing unit to enter which mode.

By an example of FIG. 6, FIG. 6 shows control signals of three pulse widths. The control signal of the first pulse may be a control signal that instructs the logic processing unit to enter the first mode. The control signal of the second pulse may be a control signal that instructs the logic processing unit to enter the second mode. The control signal of the third pulse may be a control signal that instructs the logic processing unit to enter the third mode.

T is a unit time, for example, T=1 μs.

When there is a high level pulse with a duration less than 0.5 T (including a pulse with a duration of zero, that is, the Ctrl pin is in a normally-low logic state) at the Ctrl pin, it may be understood as that the logic processing unit 17 detects a control signal of the first pulse, and in this case the detection operational amplifier module 1 may enter the first mode.

When there is a high level pulse with a duration greater than 2 T (including a pulse with an extremely long duration, that is, the Ctrl pin is in a normally-high logic state) at the Ctrl pin, it may be understood as that the logic processing unit 17 detects a control signal of the second pulse, and in this case the detection operational amplifier module 1 may enter the second mode.

When there is a high level pulse with a duration greater than 0.5 T and less than 2 T at the Ctrl pin, it may be understood as that the logic processing unit 17 detects a control signal of the third pulse, and in this case the detection operational amplifier module 1 may enter the third mode.

In other solutions, correspondences between the three modes and different pulse widths may not be limited to the foregoing examples. In addition, in further combination with the enabling control of the buffer, the types of modes are not limited thereto.

In conclusion of the above description, in combination with FIG. 5, the optional solutions have the following special improvements.

1. The switch combination composed of the first switch S1, the second switch S2, and the third switch S3 is used to construct the straight-through channel between the IN+ pin and the OUT pin of the detection operational amplifier module 1. When the first switch S1 is turned off and the second switch S2 and the third switch S3 are turned on, a direct connection from the IN+ pin to the OUT pin is implemented. Operating parameters of the switch are not affected by the first buffer 13 (the first switch S1 is turned off at this time), and the main operational amplifier 12 is certainly disabled at this time. The chip of the detection operational amplifier module 1 may not enable both the function of the detection channel switch and the operating mode of the main operational amplifier.

2. When the main operational amplifier 12 is enabled, the second switch S2 and the third switch S3 may be turned off. In this case, the first switch S1 may be turned on, and with the properties of the operational amplifier of the first buffer (especially the unity gain buffer), two terminals of the second switch S2 are enabled to be respectively connected to the B1 IN+ pin and the B1 IN− pin of the first buffer 13 (which may be implemented by turning on the first switch S1), so that a voltage difference at two terminals of the second switch S2 is extremely small (for example, 1 mV) when the second switch S2 is turned off. Meanwhile, a large turned-on resistance (for example, 100 KΩ) switch that an independent switch chip does not use may be adopted, to further ensure that a turned-off impedance reaches a larger level, typically, a level of 10 GΩ, when the second switch S2 is turned off, thereby implementing minimization of a turned-off leakage current of the channel of the second switch S2. Finally, an entire input leakage current of the main operational amplifier 12 during operating is ensured to be minimized.

3. By determining a pulse width, receiving, by one control pin, input commands of three different operating modes is implemented.

An embodiment of the present invention further provides an electronic device, including the detection circuit for a connection impedance described above in the optional solutions.

Eventually, it should be noted that the aforementioned embodiments are only used to illustrate the technical solutions of the present invention, but not to limit the present invention. Although the present invention has been described in detail with reference to the foregoing embodiments, a person of ordinary skill in the art shall understand that modifications may be made to the technical solutions described in the foregoing embodiments, or some or all of the technical features thereof may be equivalently substituted. However, these modifications or substitutions do not essentially depart the corresponding technical solutions from the scope of the technical solutions of the embodiments of the present invention.

What is claimed is:

1. A detection circuit for a connection impedance, comprising: a detection operational amplifier module, wherein the detection operational amplifier module comprises: a first buffer, a switch unit, and a main operational amplifier;
   a first input terminal of the first buffer is connected to a first acquisition electrode through a first front-end circuit, an output terminal of the main operational amplifier is connected to a back-end circuit, and an output terminal of the first buffer is connected to a second input terminal of the first buffer;
   a first terminal of the switch unit is directly or indirectly connected to the first front-end circuit, and a second terminal of the switch unit is connected to the back-end circuit; and
   the switch unit is configured to: control the first front-end circuit to be directly connected to the back-end circuit, to form a turned-on straight-through channel, or control the straight-through channel to be turned off, wherein the main operational amplifier stops operating when the turned-on straight-through channel is formed.

2. The detection circuit for a connection impedance according to claim 1, wherein the detection operational amplifier module further comprises: a first electro-static discharge unit; and the first input terminal and the second input terminal of the first buffer are further grounded through the first electro-static discharge unit.

3. The detection circuit for a connection impedance according to claim 2, wherein the switch unit comprises a first switch, a second switch, and a third switch; a first terminal of the first switch is connected to the output terminal of the first buffer, a first terminal of the second switch is connected to the first front-end circuit and the first input terminal of the first buffer, a second terminal of the second switch is connected to a first terminal of the third switch, a second terminal of the third switch is connected to the back-end circuit, and a second terminal of the first switch is connected to a connection point between the second switch and the third switch; and
   the detection operational amplifier module further comprises: a logic processing unit; and the logic processing unit is connected to a controlled terminal of the first switch, a controlled terminal of the second switch, and a controlled terminal of the third switch.

4. The detection circuit for a connection impedance according to claim 1, wherein an enable terminal of the main operational amplifier and the switch unit are connected to a logic processing unit, and the logic processing unit is configured to:
   if being controlled in a first mode, control the straight-through channel to be turned off, and disable a function of the main operational amplifier;
   if being controlled in a second mode, enable a function of the main operational amplifier, and control the straight-through channel to be turned off; or
   if being controlled in a third mode, control the straight-through channel to be turned on, and disable a function of the main operational amplifier.

5. The detection circuit for a connection impedance according to claim 4, further comprising: a control module, wherein the logic processing unit is connected to the control module, to enter a corresponding mode in response to a control signal sent by the control module.

6. The detection circuit for a connection impedance according to claim 1, further comprising a control module, the control module being configured to directly or indirectly control an enable terminal of the main operational amplifier, and the switch unit, wherein the control module is specifically configured to:
   in a case that the turned-on straight-through channel is formed and the main operational amplifier stops operating, if the turned-on straight-through channel detects that there is an object to be tested being connected to the first acquisition electrode, control the straight-through channel to be turned off, and control the main operational amplifier to be enabled.

7. The detection circuit for a connection impedance according to claim 1, wherein the detection operational amplifier module further comprises a second buffer and a second electro-static discharge unit;
   a first input terminal of the second buffer is connected to a second acquisition electrode through a second front-end circuit, and an output terminal of the second buffer is connected to a second input terminal of the second buffer; and
   the first input terminal and the second input terminal of the second buffer are further grounded through the second electro-static discharge unit.

8. The detection circuit for a connection impedance according to claim 7, wherein the first buffer and the second buffer each are a unity gain buffer.

9. The detection circuit for a connection impedance according to claim 1, wherein the detection operational amplifier module is disposed in a same chip.

10. An electronic device, comprising the detection circuit for a connection impedance according to claim 1.

11. The detection circuit for a connection impedance according to claim 2, wherein the detection operational amplifier module further comprises a second buffer and a second electro-static discharge unit;

a first input terminal of the second buffer is connected to a second acquisition electrode through a second front-end circuit, and an output terminal of the second buffer is connected to a second input terminal of the second buffer; and the first input terminal and the second input terminal of the second buffer are further grounded through the second electro-static discharge unit.

12. The detection circuit for a connection impedance according to claim 3, wherein the detection operational amplifier module further comprises a second buffer and a second electro-static discharge unit;

a first input terminal of the second buffer is connected to a second acquisition electrode through a second front-end circuit, and an output terminal of the second buffer is connected to a second input terminal of the second buffer; and the first input terminal and the second input terminal of the second buffer are further grounded through the second electro-static discharge unit.

13. The detection circuit for a connection impedance according to claim 4, wherein the detection operational amplifier module further comprises a second buffer and a second electro-static discharge unit;

a first input terminal of the second buffer is connected to a second acquisition electrode through a second front-end circuit, and an output terminal of the second buffer is connected to a second input terminal of the second buffer; and the first input terminal and the second input terminal of the second buffer are further grounded through the second electro-static discharge unit.

14. The detection circuit for a connection impedance according to claim 5, wherein the detection operational amplifier module further comprises a second buffer and a second electro-static discharge unit;

a first input terminal of the second buffer is connected to a second acquisition electrode through a second front-end circuit, and an output terminal of the second buffer is connected to a second input terminal of the second buffer; and the first input terminal and the second input terminal of the second buffer are further grounded through the second electro-static discharge unit.

15. The detection circuit for a connection impedance according to claim 6, wherein the detection operational amplifier module further comprises a second buffer and a second electro-static discharge unit;

a first input terminal of the second buffer is connected to a second acquisition electrode through a second front-end circuit, and an output terminal of the second buffer is connected to a second input terminal of the second buffer; and the first input terminal and the second input terminal of the second buffer are further grounded through the second electro-static discharge unit.

16. The electronic device according to claim 10, wherein the detection operational amplifier module further comprises: a first electro-static discharge unit; and the first input terminal and the second input terminal of the first buffer are further grounded through the first electro-static discharge unit.

17. The electronic device according to claim 16, wherein the switch unit comprises a first switch, a second switch, and a third switch; a first terminal of the first switch is connected to the output terminal of the first buffer, a first terminal of the second switch is connected to the first front-end circuit and the first input terminal of the first buffer, a second terminal of the second switch is connected to a first terminal of the third switch, a second terminal of the third switch is connected to the back-end circuit, and a second terminal of the first switch is connected to a connection point between the second switch and the third switch; and the detection operational amplifier module further comprises: a logic processing unit; and the logic processing unit is connected to a controlled terminal of the first switch, a controlled terminal of the second switch, and a controlled terminal of the third switch.

18. The electronic device according to claim 10, wherein an enable terminal of the main operational amplifier and the switch unit are connected to a logic processing unit, and the logic processing unit is configured to:

if being controlled in a first mode, control the straight-through channel to be turned off, and disable a function of the main operational amplifier;

if being controlled in a second mode, enable a function of the main operational amplifier, and control the straight-through channel to be turned off; or if being controlled in a third mode, control the straight-through channel to be turned on, and disable a function of the main operational amplifier.

19. The electronic device according to claim 18, further comprising: a control module, wherein the logic processing unit is connected to the control module, to enter a corresponding mode in response to a control signal sent by the control module.

20. The electronic device according to claim 10, further comprising a control module, the control module being configured to directly or indirectly control an enable terminal of the main operational amplifier, and the switch unit, wherein the control module is specifically configured to:

in a case that the turned-on straight-through channel is formed and the main operational amplifier stops operating, if the turned-on straight-through channel detects that there is an object to be tested being connected to the first acquisition electrode, control the straight-through channel to be turned off, and control the main operational amplifier to be enabled.

\* \* \* \* \*